US009861369B2

United States Patent
Delgado et al.

(10) Patent No.: US 9,861,369 B2
(45) Date of Patent: Jan. 9, 2018

(54) METHOD AND APPARATUS FOR TREATING A PATIENT BY INTENTIONALLY OCCLUDING A BLOOD VESSEL, INCLUDING METHOD AND APPARATUS FOR INDUCING WEIGHT LOSS IN A PATIENT BY INTENTIONALLY OCCLUDING THE CELIAC ARTERY

(71) Applicant: Anaxiom Corporation, Laguna Hills, CA (US)

(72) Inventors: Reynolds M. Delgado, Bellaire, TX (US); William E. Cohn, Bellaire, TX (US)

(73) Assignee: Anaxiom Corporation, Laguna Hills, CA (US)

( * ) Notice: Subject to any disclaimer, the term of this patent is extended or adjusted under 35 U.S.C. 154(b) by 4 days.

(21) Appl. No.: 13/655,354

(22) Filed: Oct. 18, 2012

(65) Prior Publication Data
US 2013/0096580 A1    Apr. 18, 2013

Related U.S. Application Data

(60) Provisional application No. 61/548,432, filed on Oct. 18, 2011.

(51) Int. Cl.
*A61B 17/12*    (2006.01)
*A61F 5/00*    (2006.01)
*A61B 17/122*    (2006.01)

(52) U.S. Cl.
CPC .......... *A61B 17/12* (2013.01); *A61B 17/1204* (2013.01); *A61B 17/12031* (2013.01);
(Continued)

(58) Field of Classification Search
CPC .... A61B 17/12022; A61B 2017/12018; A61B 17/12; A61F 5/005; A61F 2/02;
(Continued)

(56) References Cited

U.S. PATENT DOCUMENTS 5,382,261 A     1/1995  Palmaz
5,522,882 A *   6/1996  Gaterud et al. .............. 623/1.11
(Continued)

FOREIGN PATENT DOCUMENTS

EP    1707233        10/2006
EP    1707233 A2 *  10/2006
(Continued)

OTHER PUBLICATIONS

Sllveira LA, Arterial diameter of the celiac trunk and its branches: Anatomical study, Jan. 24, 2009, Acta Cirurgica Brasileria, vol. 24, pp. 43-47.*

(Continued)

*Primary Examiner* — Christopher L Templeton
*Assistant Examiner* — George J Ulsh
(74) *Attorney, Agent, or Firm* — Knobbe Martens Olson and Bear LLP

(57) ABSTRACT

A method for inducing weight loss in a patient, the method comprising:
intentionally occluding a blood vessel so as to create hypoperfusion in a gastrointestinal organ serviced by the blood vessel, whereby to interfere with normal gastrointestinal function and thereby induce weight loss in a patient.

12 Claims, 16 Drawing Sheets

(52) U.S. Cl.
CPC .. *A61B 17/12036* (2013.01); *A61B 17/12109* (2013.01); *A61B 17/12136* (2013.01); *A61B 17/12145* (2013.01); *A61B 17/12172* (2013.01); *A61F 5/0013* (2013.01); *A61B 17/122* (2013.01); *A61B 17/12013* (2013.01)

(58) Field of Classification Search
CPC .... A61F 2/04; A61F 2/95; A61F 2/954; A61F 2/958; A61M 25/104; A61M 25/10
USPC ....... 606/157, 158, 191, 192, 193, 194, 213; 623/1.11, 1.12, 1.23
See application file for complete search history.

(56) References Cited

U.S. PATENT DOCUMENTS

| | | | |
|---|---|---|---|
| 6,179,878 B1* | 1/2001 | Duerig et al. | 128/898 |
| 6,942,680 B2* | 9/2005 | Grayzel et al. | 606/194 |
| 7,998,220 B2* | 8/2011 | Murphy | 623/23.64 |
| 8,162,970 B2* | 4/2012 | Gilson et al. | 606/200 |
| 2003/0187474 A1* | 10/2003 | Keegan | A61F 2/0095 606/200 |
| 2004/0044351 A1 | 3/2004 | Searle | |
| 2004/0093058 A1* | 5/2004 | Cottone et al. | 623/1.11 |
| 2008/0027481 A1* | 1/2008 | Gilson et al. | 606/200 |
| 2008/0312679 A1* | 12/2008 | Hardert et al. | 606/194 |
| 2009/0318749 A1 | 12/2009 | Shuros et al. | |
| 2010/0185220 A1* | 7/2010 | Naghavi et al. | 606/158 |
| 2013/0013084 A1* | 1/2013 | Birk | A61F 5/0079 623/23.68 |

FOREIGN PATENT DOCUMENTS

| | | |
|---|---|---|
| WO | WO 98/46115 A2 | 10/1998 |
| WO | WO 2005/074844 A1 | 8/2005 |
| WO | WO 2005/074845 A1 | 8/2005 |
| WO | WO 2007/006139 A1 | 1/2007 |
| WO | WO 2008/022327 A2 | 2/2008 |

OTHER PUBLICATIONS

European Search Report for application No. EP 12842548.5 dated Nov. 25, 2014, 5 pages.
International Preliminary Report on Patentability re International Application No. PCT/US2012/060905 dated May 1, 2014, in 7pages.
International Search Report and Written Opinion re International Application No. PCT/US2012/060905 dated Feb. 21, 2013, in 9 pages.

* cited by examiner

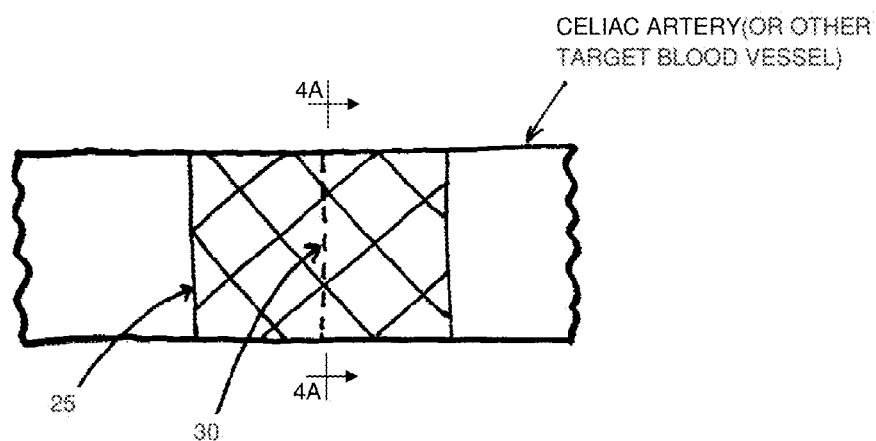
FIG. 4
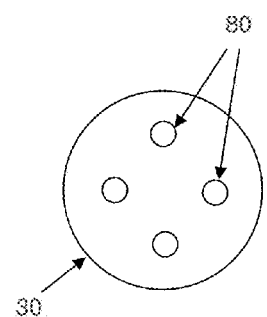
FIG. 4A
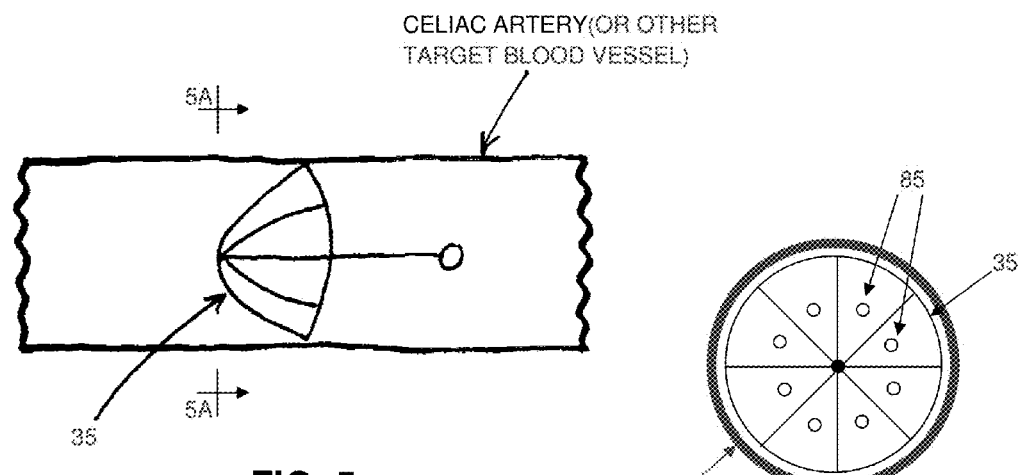
FIG. 5
FIG. 5A

METHOD AND APPARATUS FOR TREATING A PATIENT BY INTENTIONALLY OCCLUDING A BLOOD VESSEL, INCLUDING METHOD AND APPARATUS FOR INDUCING WEIGHT LOSS IN A PATIENT BY INTENTIONALLY OCCLUDING THE CELIAC ARTERY

REFERENCE TO PENDING PRIOR PATENT APPLICATION

This patent application claims benefit of prior U.S. Provisional Patent Application Ser. No. 61/548,432, filed Oct. 18, 2011 by William E. Cohn et al. for METHOD AND APPARATUS FOR INDUCING WEIGHT LOSS IN A PATIENT BY INTENTIONALLY OCCLUDING THE CELIAC ARTERY, which patent application is hereby incorporated herein by reference.

FIELD OF THE INVENTION

This invention relates to surgical methods and apparatus in general, and more particularly to surgical and non-surgical methods and apparatus for treating a patient by intentionally occluding a blood vessel, including a catheter-based method and apparatus for inducing weight loss in a patient by intentionally occluding the celiac artery.

BACKGROUND OF THE INVENTION

Obesity is a serious medical condition. Complications associated with obesity include hypertension, diabetes, coronary artery disease, stroke, congestive heart failure, multiple orthopedic problems, pulmonary insufficiency, etc. Obesity can significantly affect quality of life and can result in a markedly decreased life expectancy.

To date, surgery is the only proven method for inducing substantial long-term weight loss in a patient. Numerous surgical procedures and devices have been developed to induce such weight loss, e.g., "stomach stapling", the Roux-en-Y ("The Roux") bypass procedure, the vertical banded gastroplasty ("VBG") procedure, etc. However, all of the known surgical procedures and devices developed to date for inducing weight loss in a patient suffer from one or more significant disadvantages.

Accordingly, a new method and apparatus is needed for inducing weight loss in a patient.

SUMMARY OF THE INVENTION

The present invention provides a novel method and apparatus for inducing weight loss in a patient by intentionally occluding the celiac artery.

The present invention also provides a novel method and apparatus for inducing weight loss in a patient by intentionally occluding a blood vessel other than the celiac artery, and/or in addition to the celiac artery.

And the present invention provides a novel method and apparatus for treating a patient for purposes other than inducing weight loss in the patient by intentionally occluding a blood vessel.

In one preferred form of the present invention, there is provided a method for inducing weight loss in a patient, the method comprising:

intentionally occluding a blood vessel so as to create hypoperfusion in a gastrointestinal organ serviced by the blood vessel, whereby to interfere with normal gastrointestinal function and thereby induce weight loss in a patient.

In another preferred form of the present invention, there is provided apparatus for occluding a blood vessel comprising a two-part composite stent occluder comprising (i) an exterior, endothelializing support stent, and (ii) an interior, occluding stent comprising a loose weave fabric windsock.

In another preferred form of the present invention, there is provided apparatus for occluding a blood vessel comprising a two-part composite stent occluder comprising (i) an exterior, endothelializing support stent, and (ii) an interior, progressively-occluding element.

In another preferred form of the present invention, there is provided a method for providing treatment to a patient, the method comprising:

intentionally occluding a blood vessel so as to create hypoperfusion in tissue serviced by the blood vessel, whereby to interfere with tissue function and thereby treat the patient.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 4 is a schematic view showing an occluding stent for occluding the celiac artery (or other target blood vessel) and thereby inducing weight loss in a patient;

FIG. 4A is a sectional view taken along line 4A-4A of FIG. 4;

FIG. 5 is a schematic view showing an occluding umbrella device for occluding the celiac artery (or other target blood vessel) and thereby inducing weight loss in a patient;

FIG. 5A is a sectional view taken along line 5A-5A of FIG. 5;

DETAILED DESCRIPTION OF THE PREFERRED EMBODIMENTS

The present invention provides a novel method and apparatus for inducing weight loss in a patient by intentionally occluding the celiac artery.

The present invention also provides a novel method and apparatus for inducing weight loss in a patient by intentionally occluding a blood vessel other than the celiac artery, and/or in addition to the celiac artery.

And the present invention provides a novel method and apparatus for treating a patient for purposes other than inducing weight loss in the patient by intentionally occluding a blood vessel.

Inducing Weight Loss in a Patient by Intentionally Occluding the Celiac Artery and/or Other Blood Vessels In one preferred form of the present invention, weight loss is induced in a patient by intentionally occluding the celiac artery in order to create hypoperfusion in the stomach, whereby to induce weight loss in the patient.

More particularly, the celiac artery supplies oxygenated blood to the stomach, liver, pancreas, spleen and to the superior half of the duodenum. The celiac artery is a major source of blood for the stomach, inasmuch as the other blood vessels supplying nourishment to the stomach provide adequate flow to maintain viability, but cannot provide the marked increase in blood flow seen in the post-prandial period.

Figure 1:
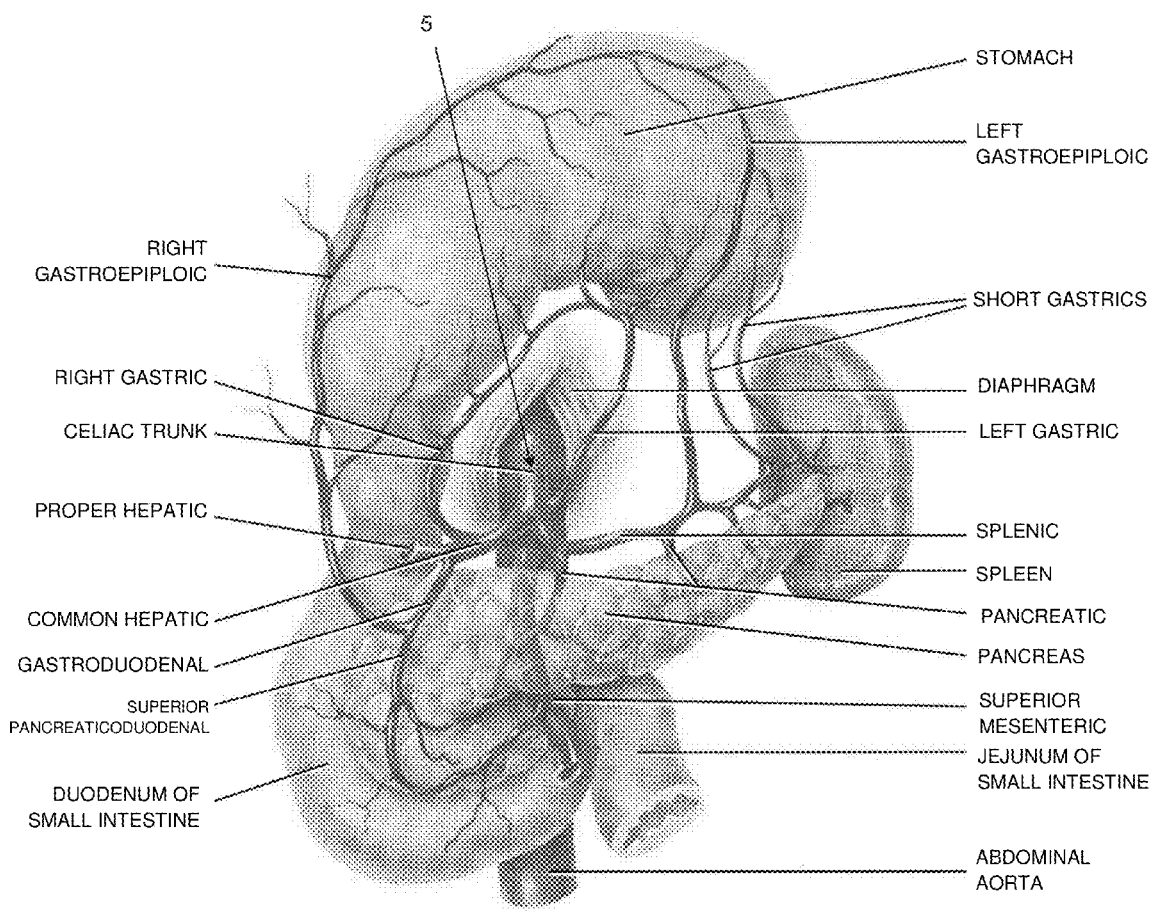
FIG. 1 is a schematic view showing one preferred location for occluding the celiac artery in order to induce weight loss in a patient.

Accordingly, in one form of the present invention, the celiac artery is intentionally reversibly occluded gradually over time in order to create hypoperfusion in the stomach (and/or other gastrointestinal organs serviced by the celiac artery) so as to interfere with normal gastrointestinal function and thereby induce weight loss in the patient. Occlusion is preferably effected at a location where it will only interfere with gastrointestinal function and will not seriously impede other essential anatomical functions. By way of example but not limitation, and looking now at FIG. 1, occlusion may be effected in the trunk of the celiac artery, e.g., at the location 5 shown in FIG. 1.

Alternatively, occlusion may be effected in branches of the celiac artery (e.g., the left or right gastric arteries, the left or right gastroepiploic arteries, the common hepatic artery, and/or other celiac artery branches).

Furthermore, and also in accordance with the present invention, occlusion may be intentionally induced in other blood vessels servicing the organs of the gastrointestinal tract, whereby to impede normal gastrointestinal function and thereby induce weight loss in the patient. By way of example but not limitation, occlusion may be intentionally induced in other mesenteric vessels (e.g., the superior mesenteric artery and/or its major branches), and/or mesenteric veins, etc.

In essence, the present invention comprises the intentional occlusion of substantially any blood vessel servicing the gastrointestinal tract such that the occlusion diminishes normal gastrointestinal function, whereby to induce weight loss in the patient. One preferred form of the present invention comprises the intentional occlusion of the celiac artery (including one or more of its branches) so as to diminish gastrointestinal function and thereby induce weight loss in the patient.

External Occluding Devices.

Occlusion may be effected by constricting blood flow through the target blood vessel using an external occluding device, i.e., by applying an external occluding device against the outer surface of the blood vessel and causing the blood vessel to close down so as to occlude its internal lumen.

Figure 2:
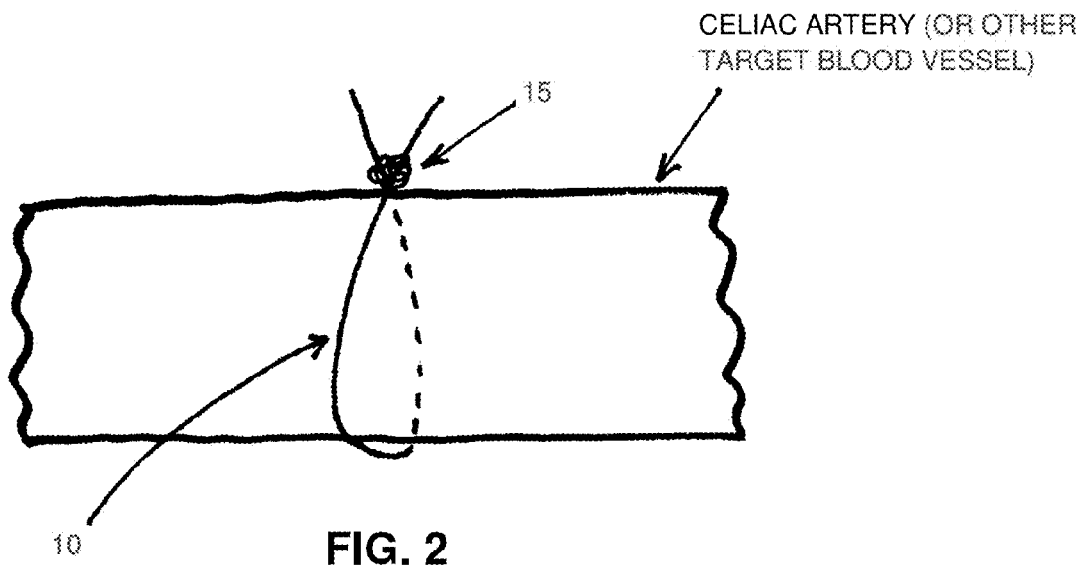
FIG. 2 is a schematic view showing a ligating suture for occluding the celiac artery (or other target blood vessel) and thereby inducing weight loss in a patient.

By way of example but not limitation, and looking now at FIG. 2, the target blood vessel may be occluded using a ligating suture 10 comprising a knot 15.

Figure 3:
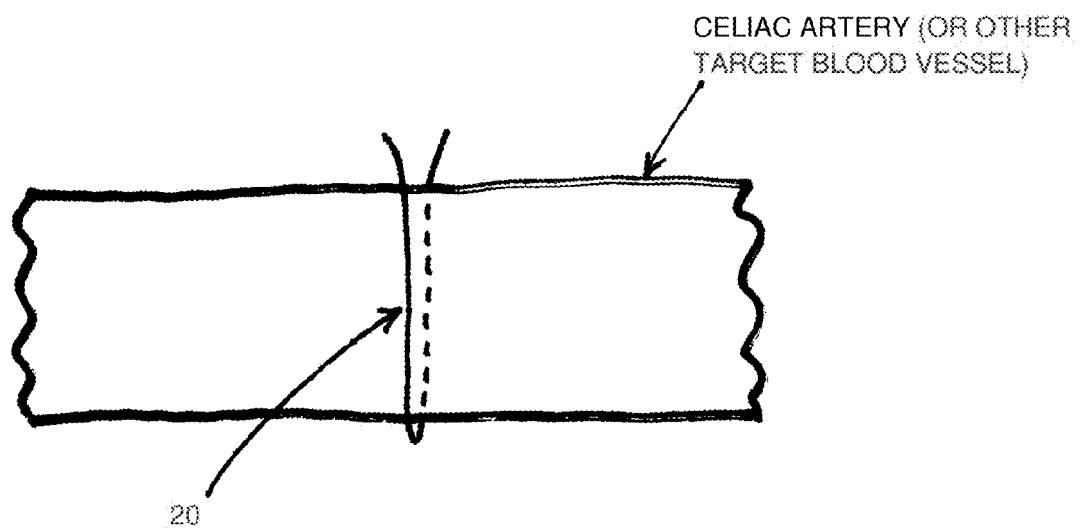
FIG. 3 is a schematic view showing a ligating clip for occluding the celiac artery (or other target blood vessel) and thereby inducing weight loss in a patient.

By way of further example but not limitation, and looking now at FIG. 3, the target blood vessel may be occluded using a ligating clip 20.

Or the target blood vessel may be occluded using other external occluding devices which will be apparent to those skilled in the art in view of the present disclosure.

With such external occluding devices, occlusion is preferably effected by deploying the external occluding device against the exterior surface of the target blood vessel via minimally invasive (e.g., laparoscopic) surgery.

Internal Occluding Devices.

Occlusion may also be effected by constricting blood flow through the target blood vessel using an internal occluding device, i.e., by deploying an internal occluding device within the internal lumen of a blood vessel so as to restrict blood flow through the internal lumen of the blood vessel.

By way of example but not limitation, and looking now at FIGS. 4 and 4A, the target blood vessel may be occluded using an occluding stent 25 which comprises an occluding element 30 which intrudes across the lumen of the blood vessel which receives the occluding stent 25.

By way of further example but not limitation, and looking now at FIGS. 5 and 5A, the target blood vessel may be occluded using an erectable "occluding umbrella" device 35 which spans the lumen of the blood vessel.

Figure 6:
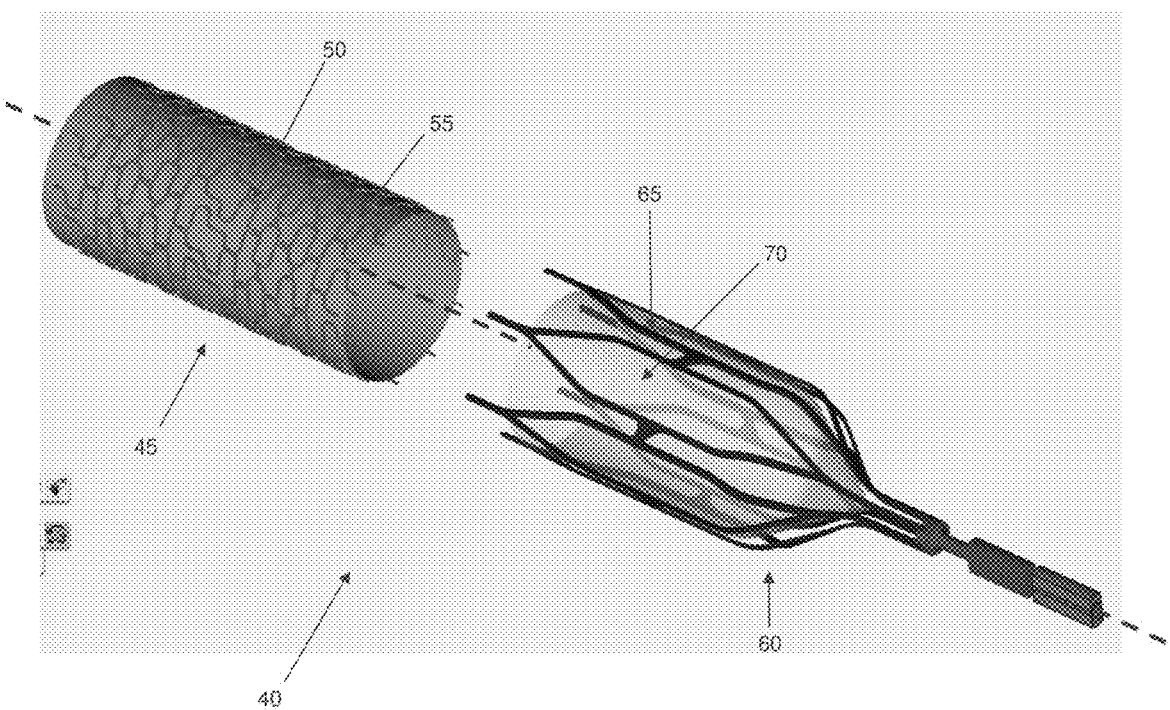
FIG. 6 is a schematic view showing a two-part composite stent occluder for occluding the celiac artery (or other target blood vessel) and thereby inducing weight loss in a patient.
Figure 7:
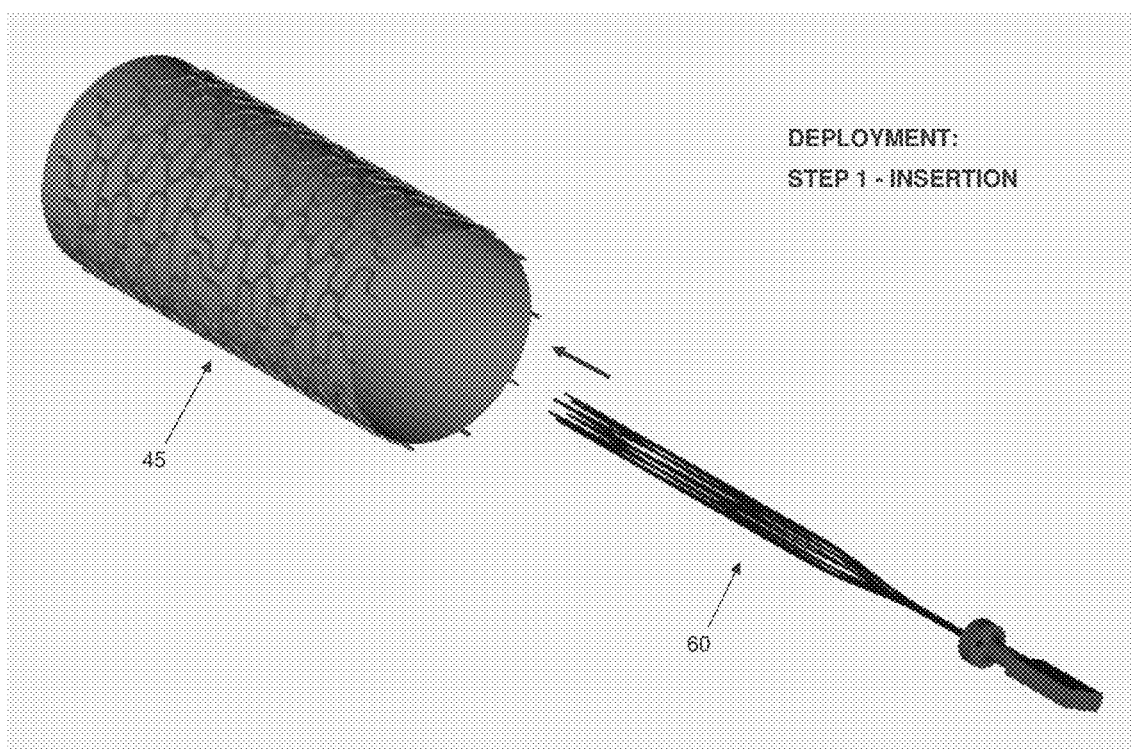
FIGS. 7-10 are schematic views showing deployment of the two-part composite stent occluder of FIG. 6.
Figure 8:
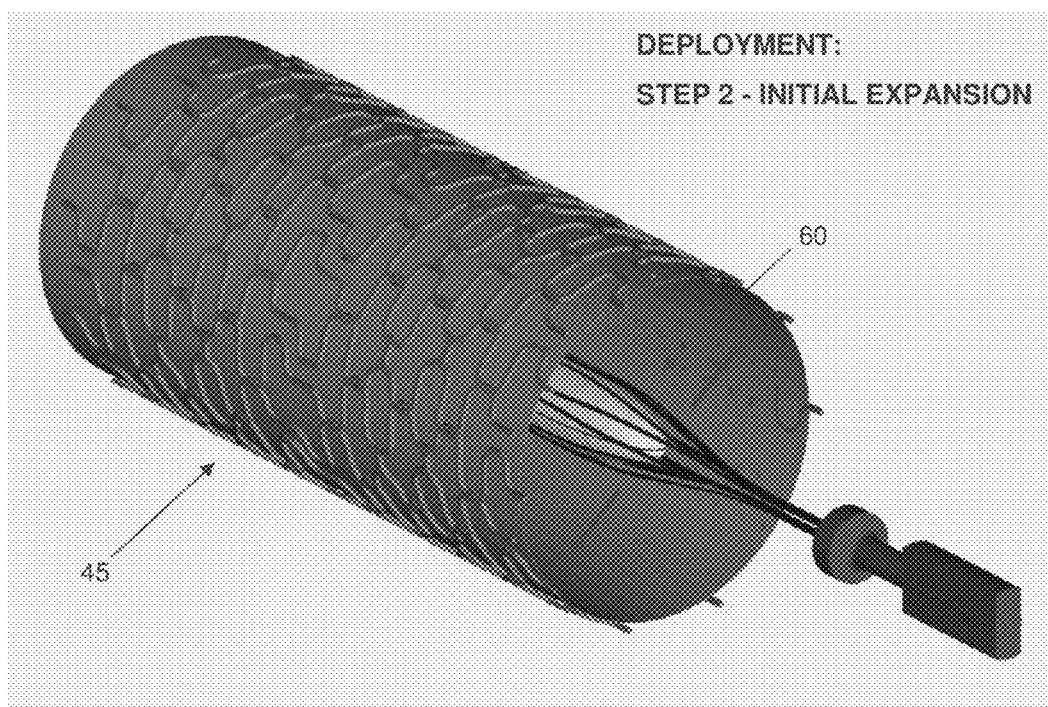
Figure 9:
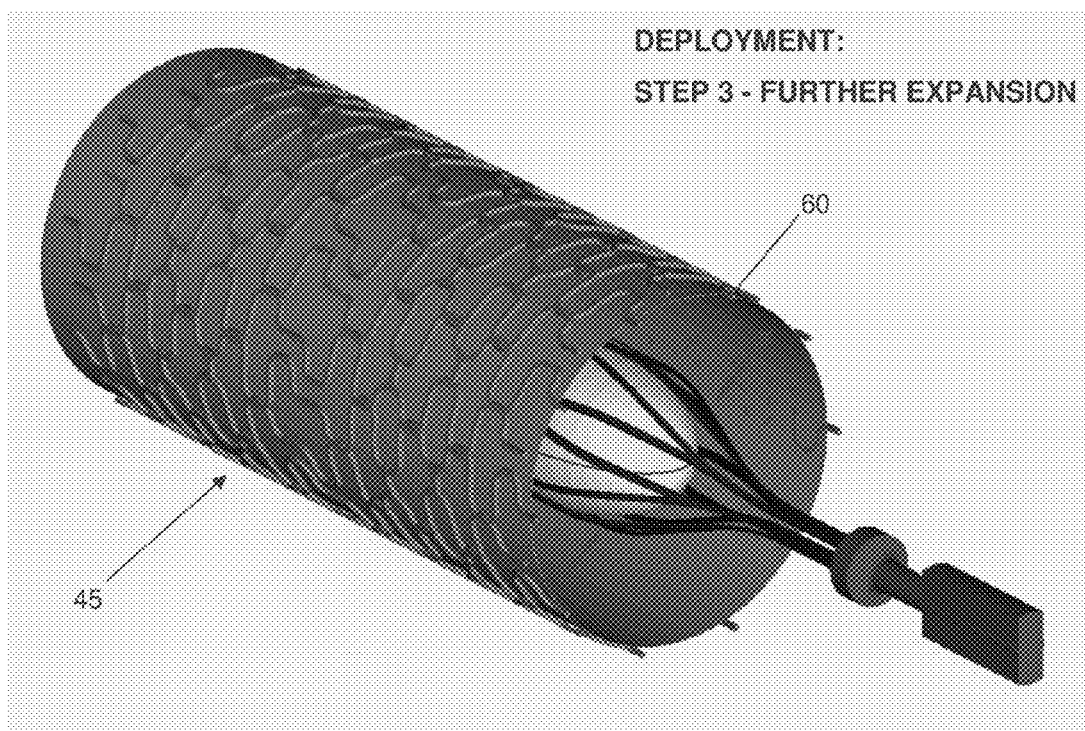
Figure 10:
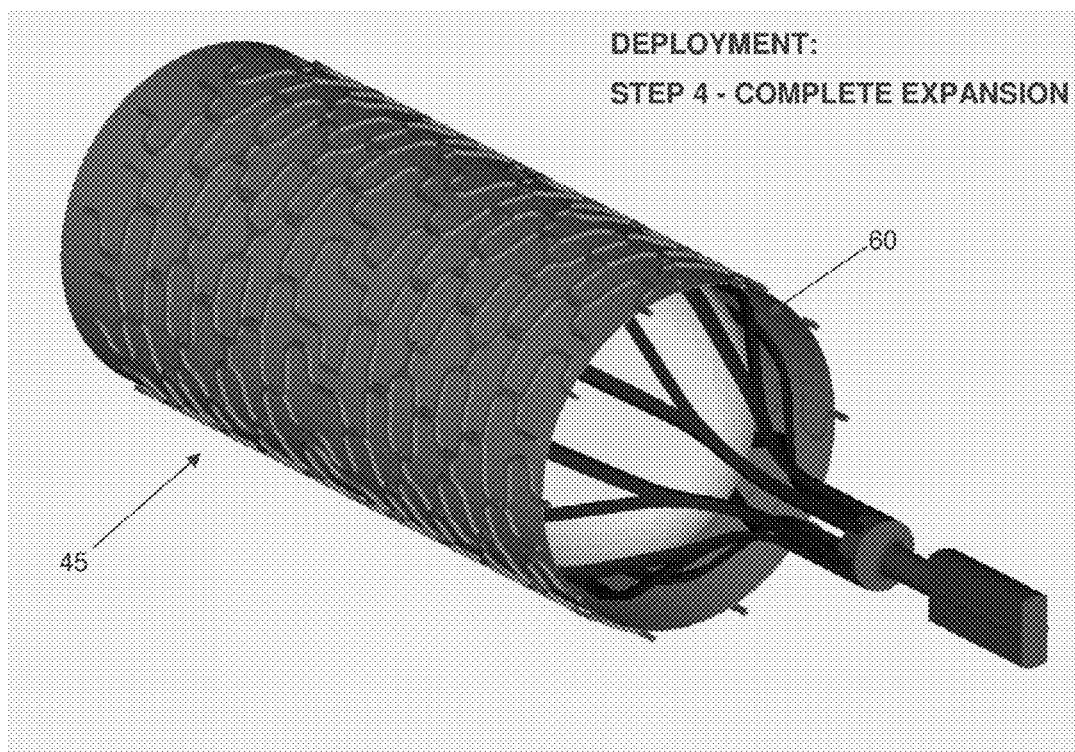
Figure 11:
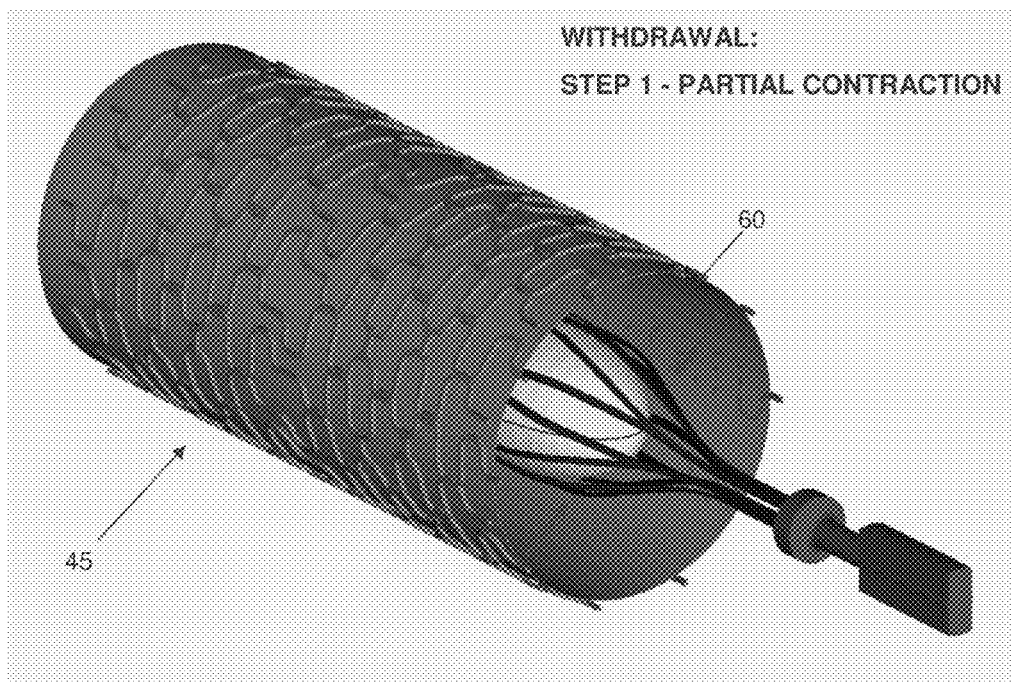
FIGS. 11-13 are schematic views showing withdrawal of the two-part composite stent occluder of FIG. 6.
Figure 12:
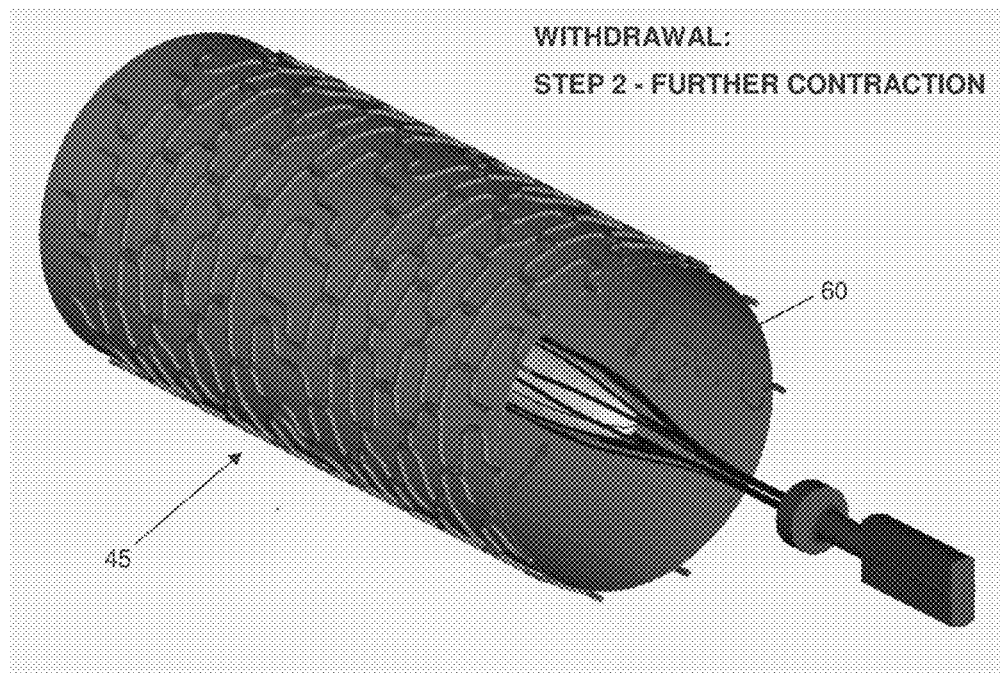
Figure 13:
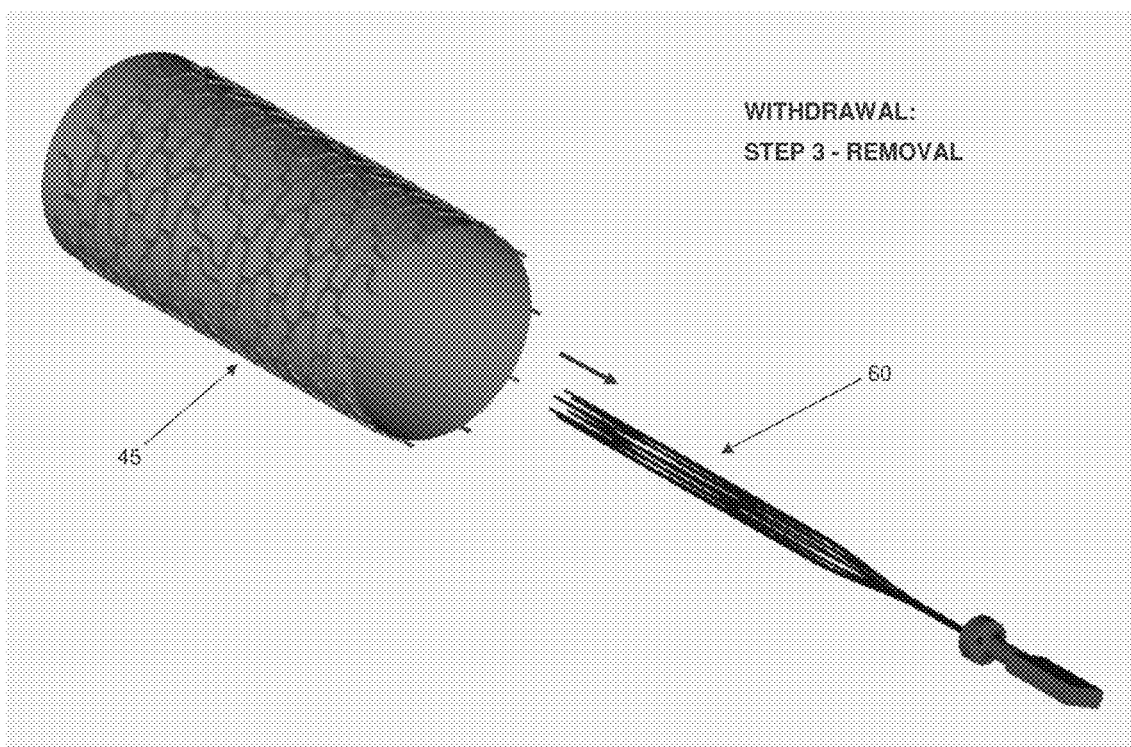

Or, and looking now at FIG. 6, the target blood vessel may be occluded using a two-part composite stent occluder 40 comprising (i) an exterior, endothelializing support stent 45 (e.g., comprising a skeleton 50 covered by fabric 55), and (ii) an interior, removable occluding stent 60 (e.g., comprising a skeleton 65 containing a loose weave fabric "windsock" 70 for clotting off with blood and thereby occluding the blood vessel). In this form of the invention, and looking now at FIGS. 7-10, the exterior endothelializing support stent 45 is deployed in the target blood vessel (e.g., the celiac artery) first, and then the interior occluding stent 60 is thereafter deployed within (and removably mounted to) the exterior endothelializing support stent 45, with the interior occluding stent 60 thereafter clotting off over time. This construction has the advantage that the interior occluding stent 60 can be readily removed from the blood vessel at a later time, whereby to restore blood flow through the blood vessel. See, for example, FIGS. 11-13, which show withdrawal of the interior occluding stent 60 from the target blood vessel (e.g., the celiac artery).

Figure 14:
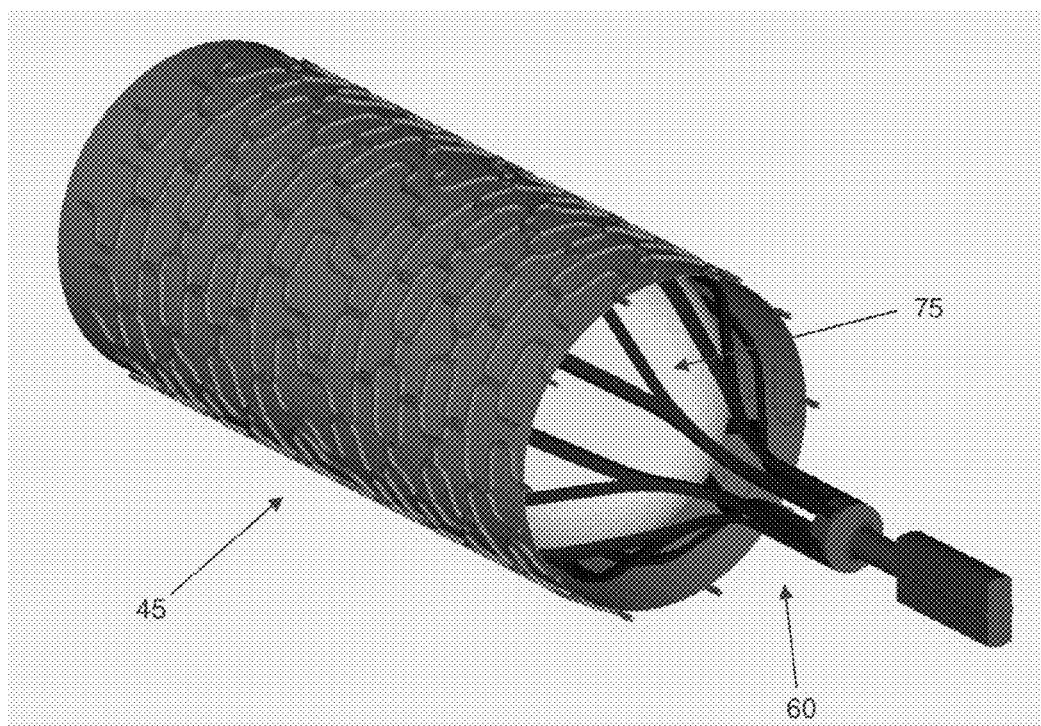
FIG. 14 is a schematic view showing a modified form of the two-part composite stent occluder of FIG. 6.

FIG. 14 shows a variation of the two-part composite stent occluder of FIGS. 6-13, wherein the interior occluding stent 60 comprises the aforementioned skeleton 65 and an inflatable occluding balloon 75 which is disposed within skeleton 65. In this form of the invention, interior occluding stent 60 is preferably removably disposed within the exterior endothelializing support stent 45.

Or the target blood vessel may be occluded using other internal occluding devices which will be apparent to those skilled in the art in view of the present disclosure.

With such internal occluding devices, occlusion is preferably effected by positioning the internal occluding device within the target blood vessel via an endoluminal approach.

Partial or Total Occlusion.

Occlusion of the target blood vessel may be partial or total. Where occlusion is to be partial, the occluding device is configured so as to permit the creation of a partial occlusion, e.g., the ligating suture 10 of FIG. 2 and/or the ligating clip 20 of FIG. 3 may be configured to apply just enough force to reduce, but not completely block, blood flow through the target blood vessel; and/or the occluding stent 25 of FIGS. 4 and 4A, and/or the erectable "occluding umbrella" device of FIGS. 5 and 5A, and/or the two-part composite stent occluder 40 of FIGS. 6-13, and/or the two part composite stent occluder 40 of FIG. 14, may be configured to reduce, but not completely block, blood flow through the target blood vessel. By way of example but not limitation, with the occluding stent 25 of FIGS. 4 and 4A, occluding element 30 may include holes 80, and with umbrella device 35 of FIGS. 5 and 5A, the umbrella device may include holes 85. Furthermore, with the two-part composite stent occluder 40 of FIGS. 6-13, the loose weave fabric "windsock" 70 may be configured to clot off only a portion of the lumen of the blood vessel, and/or with the two-part composite stent occluder 40 of FIG. 14, inflatable occluding balloon 75 may be configured to close off only a portion of the lumen of the blood vessel.

Permanent or Temporary Occlusion.

Occlusion may be permanent or temporary. Where occlusion is to be temporary, the occluding device (e.g., the ligating suture 10 of FIG. 2, the ligating clip 20 of FIG. 3, the occluding stent 25 of FIGS. 4 and 4A, the erectable "occluding umbrella" device 35 of FIGS. 5 and 5A, and/or the internal component of the two-part composite stent occluder 40 of FIGS. 6-13 and/or FIG. 14) may be configured so that the occluding device is removable at some time in the future, so that normal blood flow through the target blood vessel may be restored. Alternatively, some or all of the occluding devices may be formed out of a biodegradable or bioabsorbable material, so that the occluding device will automatically cease its occlusive function at some time in the future.

Adjusting the Degree of Occlusion Over Time.

The degree of occlusion may also be adjusted over time. By way of example but not limitation, the degree of occlusion may be increased and/or decreased over time, in order to adjust the level of hypoperfusion created in the stomach (and/or other gastrointestinal organ), whereby to selectively adjust the gastrointestinal function of the patient. Thus, if the patient is found to be losing too much weight, the degree of occlusion may be reduced so as to increase gastrointestinal function. Correspondingly, if the patient is found to be losing too little weight, the degree of occlusion may be increased so as to further decrease gastrointestinal function. By way of example but not limitation, a total occlusion may subsequently be partially re-opened or fully re-opened, a partial narrowing can be made more or less restrictive, a restrictive narrowing can be made totally occlusive, etc.

It is anticipated that different patients will require or tolerate different degrees of narrowing of the target blood vessel. It is also anticipated that patients will generally tolerate greater degrees of narrowing, or better tolerate complete occlusion, if the narrowing is established gradually. This is because gradual occlusion would allow the hypoperfused organ to produce humoral factors to recruit collateral circulation from the adjacent anatomy. This is certainly the case elsewhere in the body where vascular compromise occurs over a prolonged interval, and it is anticipated that it would also be true where occlusion is intentionally created to reduce gastrointestinal function.

Thus, an occluding device that causes slow progressive occlusion over time may be highly desirable. In one form of the invention, where the occluding device is an external occluding device, this progressive occluding device could be an encircling suture 10 (FIG. 2) and/or ligating clip 20 (FIG. 3) containing a hygroscopic material (e.g., Ameroid or the like)—the progressive occluding device could be placed laparoscopically about the exterior surface of the target blood vessel, and the hygroscopic material would then swell over time, resulting in a relatively slow, progressive occlusion of the target blood vessel. In another form of the invention, where the occluding device is an internal occluding device, the progressive occluding device could be an occluding stent 25 (FIGS. 4 and 4A) and/or an occluding umbrella device 35 containing hygroscopic material that would slowly swell over time, ultimately resulting in vessel narrowing or even complete vessel occlusion. In still another form of the invention, the progressive occluding structure could be a stent containing a diaphanous fiber mesh that slowly clots off and/or endothelializes off over time and becomes occlusive—see, for example, the interior occluding stent 60 of FIGS. 6-13, which clots off over time. In these and similar dynamic therapies, the narrowing or occlusive process is initiated at the time of intervention, but takes place over a gradual period of time, the length of which is determined by the nature, design and materials of the progressive occluding device.

Reversing Occlusion.

The ability to reverse the occlusion or narrowing of the target blood vessel may be important in many situations. In one form of the invention, where the occluding device is an external occluding device, the physician could use laparoscopic instruments to remove the externally compressive or restrictive device (e.g., the encircling suture 10 of FIG. 2, the ligating clip 20 of FIG. 3, etc.) at a time determined to optimize patient benefit and minimize adverse outcomes. In another form of the invention, where the occluding device is an internal occluding device, the physician could use catheters, wires and inflatable balloons to re-open an occluding stent (e.g., the occluding stent 25 of FIGS. 4 and 4A), occluding umbrella (e.g., the occluding umbrella device 35 of FIGS. 5 and 5A), endothelialized stent (e.g., with the two-part composite stent occluder 40 of FIGS. 6-13, or with the two-part composite stent occlude 40 of FIG. 14, the interior occluding stent could be removed), etc. In still another form of the present invention, however, the therapy would spontaneously, autonomously and progressively reverse due to the use of biodegradable or bioabsorbable components in the external occluding device and/or the internal occluding device.

In one example of a reversible intra-arterial device, the occluding device comprises the two-part composite stent occluder 40 of FIGS. 6-13 in which an exterior stent is first placed in the target blood vessel, with an interior occluding (or gradually occluding) fabric-covered stent thereafter being placed coaxially within the exterior endothelializing support stent (see FIGS. 7-10). The interface between the two components could be designed to block tissue in-growth, so that the two stents could be readily separated at a later time. During a subsequent intervention, the interior occluding stent would be removed (for example, collapsed down into a catheter) and the exterior endothelializing support stent would stay behind in the patient indefinitely (see FIGS. 11-13).

Two-Part Composite Stent Occluder Comprising Hygroscopic Material

Looking next at FIGS. 15-18, there is shown a two-part composite stent occluder 90. More particularly, and looking now at FIG. 15, two-part stent occluder 90 comprises an exterior, endothelializing support stent 95 and an interior, progressively-occluding element 100 which together form a generally tubular structure having a central lumen 105 extending therethrough.

Figure 15:
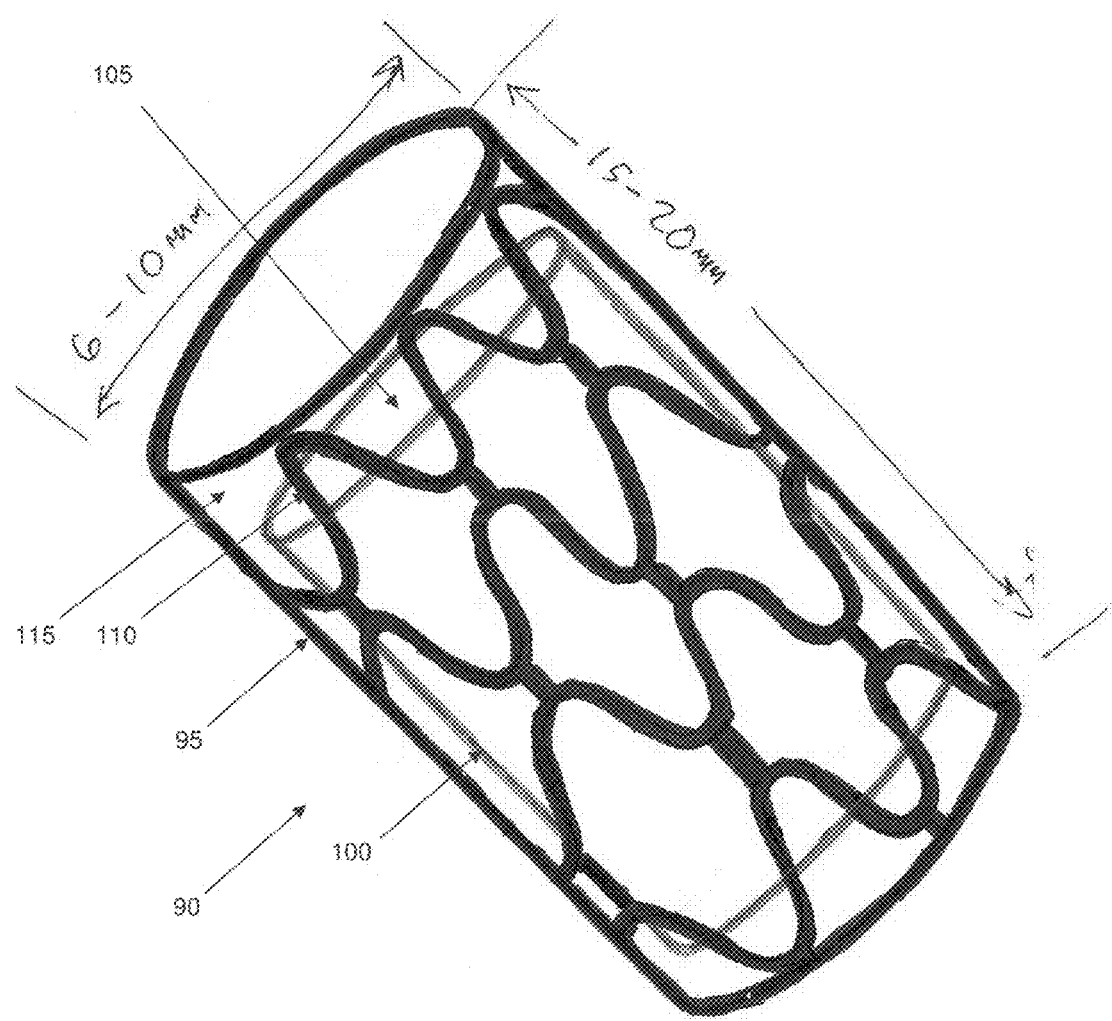
FIGS. 15 and 16 are schematic views showing another two-part composite stent occluder for occluding the celiac artery (or other target blood vessel) and thereby inducing weight loss in a patient.

Still looking now at FIG. 15, exterior, endothelializing support stent 95 preferably comprises a cylindrical Nitinol skeleton 110 covered by fabric 115.

Figure 16:
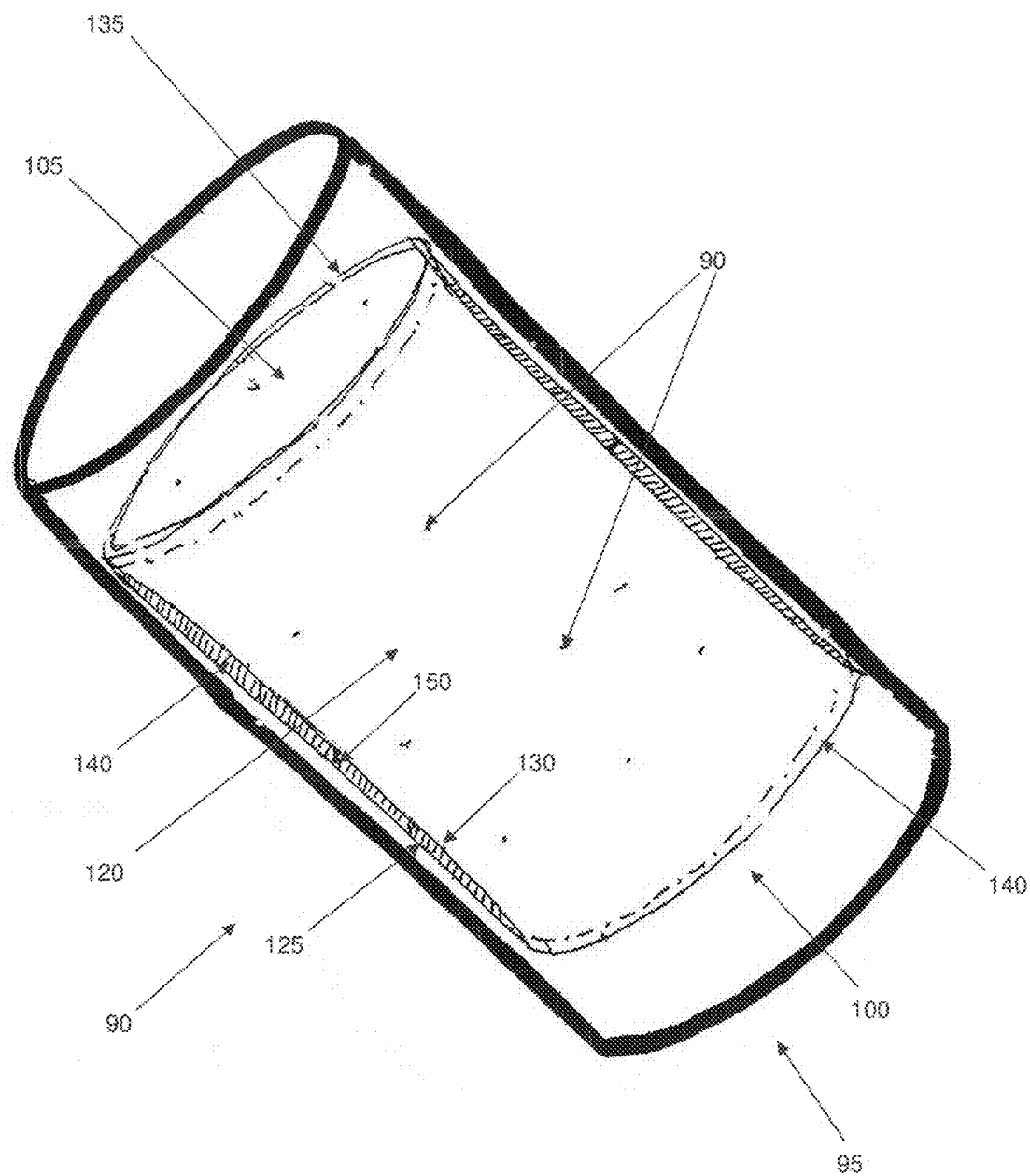

Looking next at FIGS. 15 and 16, interior, progressively-occluding element 100 preferably comprises an envelope 120 formed in the shape of a hollow cylinder and comprising (i) an exterior wall 125 connected to exterior, endothelializing support stent 95, (ii) an interior wall 130 spaced from exterior wall 125, (iii) a first end seal 135, and (iv) a second end seal 140, whereby to define a cylindrical chamber 145 between exterior and interior walls 125, 130 and first end seal 135 and second end seal 140. Chamber 145 is filled with a hygroscopic material 150 (e.g., a shape memory polymer which can absorb many times its own volume in water, so as to thereby dramatically increase in volume).

Envelope 120 is preferably formed out of a water-impermeable material such as ePTFE (e.g., 2-4 mils thick), and includes a plurality of tiny holes 155 (e.g., 0.05 mils in diameter). Tiny holes 155 permit water (but little else) to very slowly penetrate into chamber 145 and mix with hygroscopic material 150, whereby to expand the volume of the hygroscopic material 150, as will hereinafter be discussed.

Figure 17:
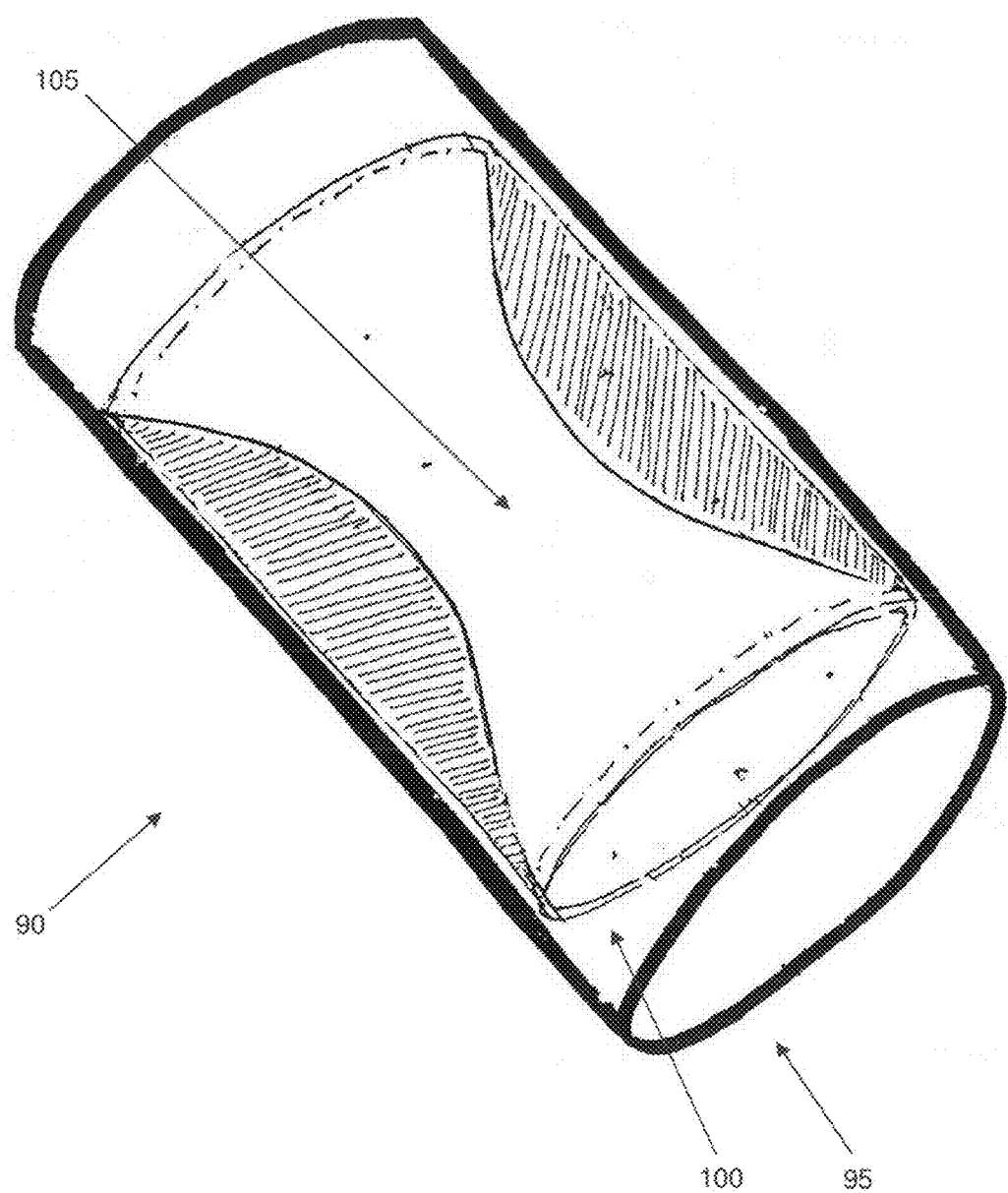
FIGS. 17 and 18 are schematic views showing the two-part composite stent occluder of FIGS. 15 and 16 closing down so as to occlude a blood vessel.
Figure 18:
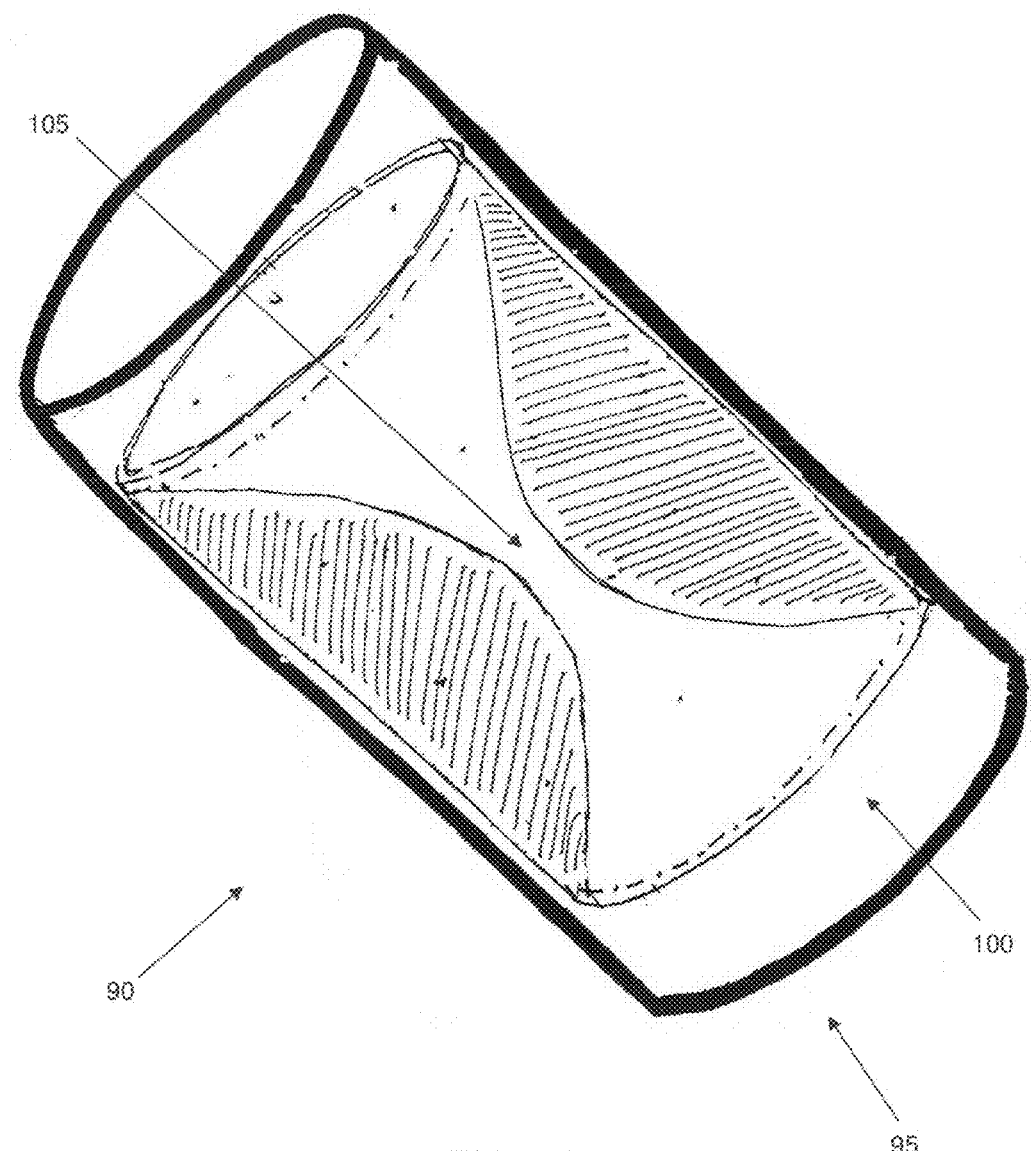

In use, and looking now at FIGS. 16-18, two-part stent occluder 90 is disposed in the lumen of the blood vessel which is to be occluded (e.g., the celiac artery) so that exterior, endothelializing support stent 95 engages and is secured to the inner wall of the blood vessel. Initially, blood passes easily through lumen central 105 of two-part stent occluder 90. However, over time, water in the blood of the patient passes through the tiny holes 155 in envelope 120 and enters chamber 145, where it contacts hygroscopic material 150. This causes the hygroscopic material 150 to slowly expand to many times its own volume, whereby to progressively occlude the central lumen 105 of two-part stent occluder 90 (see FIGS. 16-18). Thus it will be appreciated that, as a result of the foregoing construction, two-part stent occluder 90 can occlude a blood vessel so as to treat a patient (e.g., for weight loss), and this occlusion can be effected on a gradual basis.

If it should thereafter be desired to re-open the occluded blood vessel, a conventional plastically deformable balloon expandable metallic stent (not shown), or any other appropriate stent or stent-like device, may be deployed within the central lumen 105 of the occluded two-part stent occluder 90. As the conventional plastically deformable balloon expandable metallic stent is expanded, it engages the narrowed interior wall 130 of envelope 120 and drives it radially outward with substantial force. This action applies a compressive force to the water-swollen hygroscopic material 145, thereby forcing water out of the hygroscopic material 145 (e.g., in the manner of squeezing a sponge). By applying a substantial force in a rapid manner, first end seal 135 and/or second end seal 140 of envelope 120 will rupture at pre-determined zones, thereby allowing the hygroscopic material 145 to rapidly compress to its original volume, whereby to restore lumen 105 of two-part stent occluder 90 to its open condition, with the conventional plastically deformable balloon expandable metallic stent holding the lumen open.

Creating Hypoperfusion in Other Organs Via the Intentional Occlusion of Blood Vessels It should be appreciated that hypoperfusion may also be created in other organs via the intentional occlusion of blood vessels, e.g., hypoperfusion may be created in tumors via the intentional occlusion of the blood vessels servicing those tumors, in order to eradicate or reduce the tumor. In this case, the blood vessel(s) serving the tumor is (are) intentionally occluded, e.g., in the manner discussed above. Uterine fibroids, gastric and/or pancreatic tumors, bleeding gastric and/or duodenal ulcers, etc. are all candidates for the occlusion therapy of the present invention. Still other applications will be apparent to those skilled in the art in view of the present invention.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A method for inducing weight loss in a patient, the method comprising:
   intentionally occluding a blood vessel by delivering with a delivery catheter and deploying and implanting an internal occluding device at a target area within the blood vessel so as to create hypoperfusion in a gastrointestinal organ serviced by the blood vessel,
   wherein the implanted internal occluding device comprises (i) a first portion for anchoring the implanted occluding device at the target area in the blood vessel, and (ii) a second portion that remains in the blood vessel after implantation of the occluding device and removal of the delivery catheter from the blood vessel, the second portion having an inflatable balloon that at least partially occludes the blood vessel at the target area when the occluding device is implanted thereby creating the hypoperfusion.

2. The method of claim 1 wherein the blood vessel is gradually and reversibly occluded.

3. The method of claim 1 wherein the blood vessel is the celiac artery.

4. The method of claim 3 wherein the celiac artery is occluded at the trunk of the celiac artery.

5. The method of claim 1 wherein the blood vessel is selected from the group consisting of the left or right gastric arteries, the left or right gastroepiploic arteries, the common hepatic artery, and other celiac branches.

6. The method of claim 1 wherein the gastrointestinal organ is the stomach.

7. A method of inducing weight loss in a patient, the method comprising:
   delivering with a delivery catheter an occluding device to a target area within a blood vessel that supplies blood to a gastrointestinal organ;
   deploying the occluding device from the delivery catheter to implant the occluding device at the target area within the blood vessel; and
   removing the delivery catheter from the blood vessel leaving the occluding device implanted within the blood vessel,
   wherein the occluding device comprises (i) a first portion for anchoring the occluding device at the target area within the blood vessel, and (ii) a second portion comprising an inflatable balloon that at least partially occludes the blood vessel at the target area to restrict blood flow through the blood vessel.

8. The method of claim 7, wherein the blood vessel is gradually and reversibly occluded.

9. The method of claim 7, wherein the blood vessel is the celiac artery.

10. The method of claim 9, wherein the celiac artery is occluded at the trunk of the celiac artery.

11. The method of claim 7, wherein the blood vessel is selected from the group consisting of the left or right gastric arteries, the left or right gastroepiploic arteries, the common hepatic artery, and other celiac branches.

12. The method of claim 7, wherein the gastrointestinal organ is the stomach.

* * * * *

UNITED STATES PATENT AND TRADEMARK OFFICE
CERTIFICATE OF CORRECTION

PATENT NO. : 9,861,369 B2  
APPLICATION NO. : 13/655354  
DATED : January 9, 2018  
INVENTOR(S) : Reynolds M. Delgado et al.

Page 1 of 1

It is certified that error appears in the above-identified patent and that said Letters Patent is hereby corrected as shown below:

On the Title Page

In Column 2 (item (56)) at Line 12, Under Other Publications, change "Brasileria," to --Brasileira,--.

In the Specification

In Column 1 at Line 13 (approx.), After "of" insert --pending--.

In the Claims

In Column 8 at Line 52, In Claim 5, after "celiac" insert --artery--.

Signed and Sealed this  
Eighth Day of May, 2018

Andrei Iancu  
*Director of the United States Patent and Trademark Office*